(12) United States Patent
Nolan et al.

(10) Patent No.: US 7,747,330 B2
(45) Date of Patent: Jun. 29, 2010

(54) GLOBAL PARAMETER ADJUSTMENT FOR MULTIPLE STIMULATION PROGRAMS

(75) Inventors: Joseph J. Nolan, Minnetonka, MN (US); Ruth E. Bauhahn, Fridley, MN (US); Steven M. Goetz, Brooklyn Center, MN (US)

(73) Assignee: Medtronic, Inc., Minneapolis, MN (US)

( * ) Notice: Subject to any disclaimer, the term of this patent is extended or adjusted under 35 U.S.C. 154(b) by 988 days.

(21) Appl. No.: 11/372,354

(22) Filed: Mar. 9, 2006

(65) Prior Publication Data

US 2007/0213789 A1 Sep. 13, 2007

(51) Int. Cl.
*A61N 1/36* (2006.01)

(52) U.S. Cl. .................. 607/59; 607/2; 607/28; 607/30

(58) Field of Classification Search .......... 607/2, 607/30, 27, 28, 59, 62
See application file for complete search history.

(56) References Cited

U.S. PATENT DOCUMENTS

| | | | |
|---|---|---|---|
| 5,300,096 A | 4/1994 | Hall et al. | |
| 5,722,999 A | 3/1998 | Snell | |
| 5,891,178 A | 4/1999 | Mann et al. | |
| 6,308,100 B1 | 10/2001 | Er et al. | |
| 6,308,102 B1 | 10/2001 | Sieracki et al. | |
| 6,321,117 B1 | 11/2001 | Koshiol et al. | |
| 6,381,496 B1 | 4/2002 | Meadows et al. | |
| 6,440,090 B1 | 8/2002 | Schallhorn | |
| 7,062,330 B1 | 6/2006 | Boveja et al. | |
| 2003/0055406 A1* | 3/2003 | Lebel et al. ........... | 604/891.1 |
| 2004/0111131 A1 | 6/2004 | Hu et al. | |
| 2004/0199215 A1 | 10/2004 | Lee et al. | |
| 2004/0199217 A1 | 10/2004 | Lee et al. | |
| 2005/0004628 A1* | 1/2005 | Goetz et al. ........... | 607/60 |
| 2006/0229688 A1* | 10/2006 | McClure et al. ........ | 607/72 |

FOREIGN PATENT DOCUMENTS

WO WO 2006/133445 12/2006

OTHER PUBLICATIONS

"Notification of Transmittal of the International Preliminary Report on Patentability," dated Apr. 23, 2008 for corresponding PCT Application No. PCT/US2007/001767, (10 pgs.).
"Notification of Transmittal of the International Search Report and the Written Opinion of the International Search Authority, or the Declaration," dated Jun. 27, 2007 for corresponding PCT Application No. PCT/US2007/001767, (10 pgs.).

* cited by examiner

*Primary Examiner*—Carl H Layno
*Assistant Examiner*—Jennifer Stewart
(74) *Attorney, Agent, or Firm*—Shumaker & Sieffert, P.A.

(57) ABSTRACT

A user may modify a stimulation parameter in a plurality of stimulation programs with a single adjustment. During stimulation therapy, the user, such as a patient, may desire to change a parameter of the plurality of stimulation programs. The patient may press a single button on an external programmer to make the parameter change, or global adjustment, to all of the plurality of stimulation programs. This global adjustment eliminates the need for the patient to navigate through each of the plurality of stimulation programs separately and adjust the parameter. Additionally, changing the plurality of stimulation programs may be desirable for uniform stimulation therapy between programs used by the patient. The external programmer may calculate an appropriate parameter change for each stimulation program to keep parameter ratios equal between the plurality of stimulation programs.

20 Claims, 9 Drawing Sheets

GLOBAL PARAMETER ADJUSTMENT FOR MULTIPLE STIMULATION PROGRAMS

TECHNICAL FIELD

The invention relates to medical devices and, more particularly, to devices that deliver electrical stimulation.

BACKGROUND

Implantable medical devices (IMDs) may be used to deliver electrical stimulation therapy to patients to treat a variety of symptoms or conditions such as chronic pain, tremor, Parkinson's disease, epilepsy, neuralgia, urinary or fecal incontinence, sexual dysfunction, obesity, or gastroparesis. An IMD including an implantable pulse generator (IPG) may deliver stimulation therapy via implantable leads that include electrodes located proximate to the spinal cord, pelvic nerves, stomach, or brain, or elsewhere within a patient. In some cases, electrodes may be integrated with an implantable pulse generator, eliminating the need for leads. In general, the implantable medical device delivers stimulation therapy in the form of electrical stimulation pulses.

A clinician selects values for a number of programmable parameters in order to define the stimulation therapy to be delivered to a patient. For example, the clinician selects a pulse amplitude, which may be a current or voltage amplitude, a pulse width for a stimulation waveform to be delivered to the patient, as well as a rate at which the pulses are to be delivered to the patient. In addition, the clinician selects electrode combinations and polarities for delivery of the stimulation pulses. Multiple programs may be created and grouped together to provide the patient with multiple stimulation program options to treat the condition.

During stimulation therapy, the patient may use an external programmer, sometimes referred to as a patient programmer, to modify or adjust one or more parameters of a stimulation program. The patient uses a display on the external programmer to navigate and select the program to be modified and to adjust the parameter. The display may show the current parameter values associated with the program selected. The programmer transmits program or parameter changes to the IMD via wireless telemetry.

SUMMARY

The disclosure is directed to a method and system that allows a user to modify a stimulation parameter in a plurality of different stimulation programs with a single adjustment. The patient may desire to change a stimulation parameter during stimulation therapy or during an idle period in which stimulation is not being provided. The patient may enter a single command into an external programmer to make the parameter change on a "global" basis among a plurality of stimulation programs. This multi-program adjustment eliminates the need for the patient to navigate through each of the individual stimulation programs separately to adjust the parameter. Instead, the parameter may be readily adjusted across several programs simultaneously. A multi-program adjustment also may be useful in achieving more uniform stimulation therapy among multiple programs used by the patient.

The multi-program adjustment may be made according to several different methods, as predetermined by a clinician or the type of stimulation therapy. Each program may have a predetermined step value, a step value calculated based upon a remaining possible adjustment range, or a step value calculated for each stimulation program to keep parameter ratios equal between the plurality of stimulation programs during the global adjustment. The adjustment may be made to all programs loaded into a programmer or IMD, all programs within a particular program group or groups, or only to programs presently being used to deliver stimulation therapy to the patient.

In one embodiment, the disclosure provides a method comprising receiving user input specifying adjustment of a stimulation parameter for an implantable electrical stimulator, and applying the adjustment to the stimulation parameter for multiple stimulation programs applied by the electrical stimulator to deliver electrical stimulation to a patient.

In another embodiment, the disclosure provides a system comprising an implantable electrical stimulator that delivers electrical stimulation, and an external programmer that receives user input specifying adjustment of a stimulation parameter for the implantable electrical stimulator, and applies the adjustment to the stimulation parameter for multiple stimulation programs applied by the electrical stimulator to deliver electrical stimulation to a patient.

In an additional embodiment, the disclosure provides an external programmer for an implantable electrical stimulator that delivers electrical stimulation to a patient, the programmer comprising a processor configured to receive user input specifying adjustment of a stimulation parameter for the implantable electrical stimulator, and apply the adjustment to the stimulation parameter for multiple stimulation programs applied by the electrical stimulator to deliver electrical stimulation to a patient.

In a further embodiment, the disclosure provides a computer-readable medium comprising instructions to cause a processor to receive user input specifying adjustment of a stimulation parameter for an implantable electrical stimulator, and apply the adjustment to the stimulation parameter for multiple stimulation programs applied by the electrical stimulator to deliver electrical stimulation to a patient.

In various embodiments, the disclosure may provide one or more advantages. During the course of stimulation therapy, a patient may manage stimulation parameters more efficiently by changing a parameter in all programs of a group at the same time by pressing one button. This multi-program adjustment may also increase therapy efficacy by eliminating the need for the patient to change a parameter for multiple programs. The automation provided by these embodiments may allow the patient to spend less time and energy adjusting the stimulation therapy. In addition, multi-program parameter adjustment may promote greater uniformity among programs delivered by the IMD.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
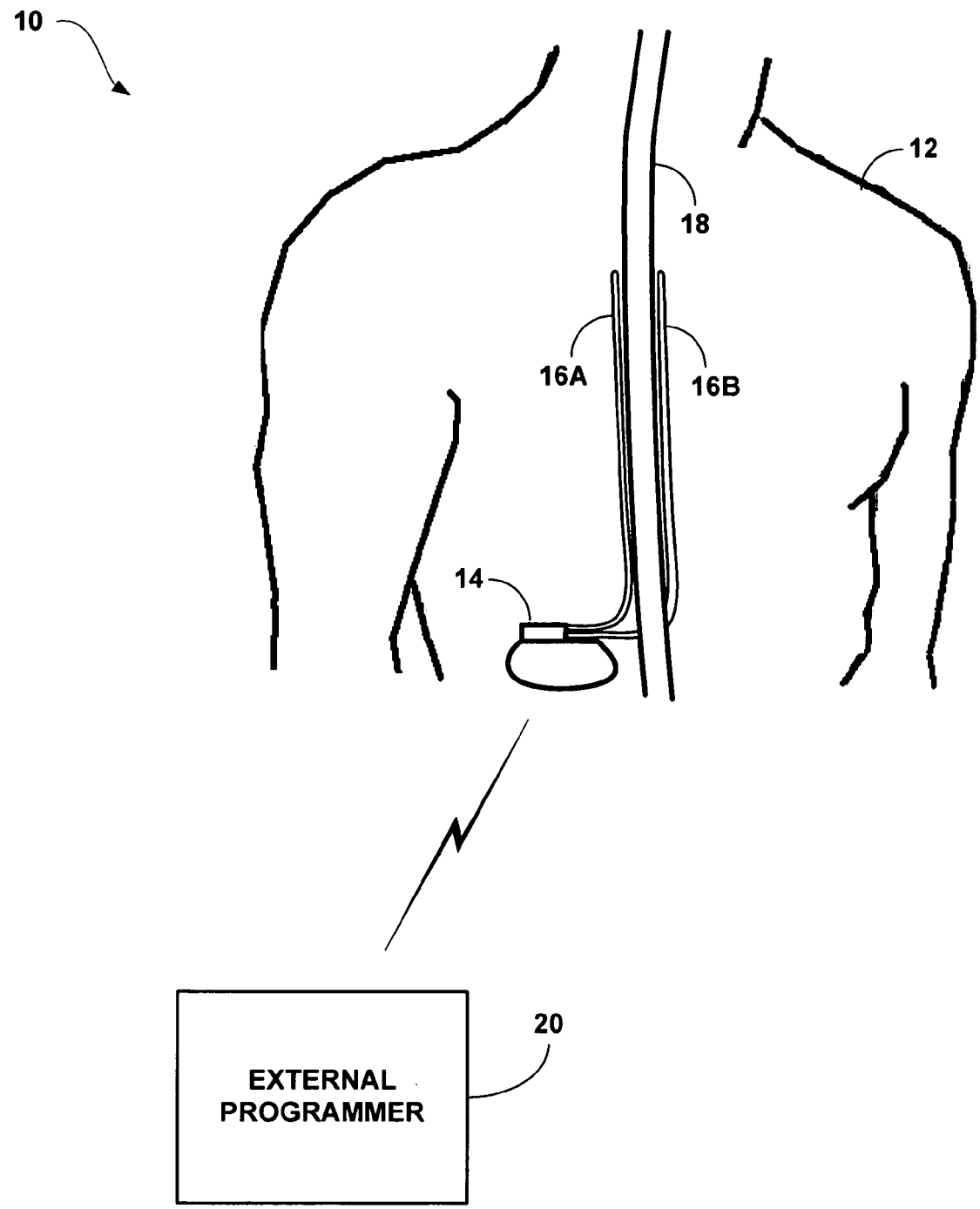
FIG. 1 is a conceptual diagram illustrating an example stimulation system with an external programmer in conjunction with a patient.

Electrical stimulation therapy may provide relief to a patient from many different conditions. Stimulation therapy is delivered based upon a variety of parameters that make up a stimulation program. Due to physiological diversity and condition differences, the parameters may vary greatly between patients. A physician may create initial parameter sets, stimulation programs, or groups of stimulation programs, when the patient begins stimulation therapy, but the patient may need to customize or adjust the parameters during therapy to find a more efficacious stimulation program or compensate for body position or therapy progression.

For example, the patient may notice that stimulation therapy is no longer providing effective relief of the condition. Alternatively, existing stimulation therapy may begin to cause undesirable side effects. In either case, the patient may desire to modify or adjust a parameter of the stimulation program to achieve greater efficacy. The patient may increase or decrease the voltage amplitude parameter to a level where stimulation therapy returns to previous efficacious levels. As further examples, the patient may increase or decrease pulse rate or pulse width.

In accordance with this disclosure, an external programmer may respond to a parameter adjustment by adjusting the parameter in multiple programs. This multi-program adjustment eliminates the need for the patient to manually adjust the amplitude for each individual stimulation program. Instead, multi-program adjustment permits a global adjustment of a parameter or parameters across multiple programs. Although a single parameter adjustment results in a multi-program adjustment of the parameter, the actual magnitude of the adjustment may be different for different programs. In particular, the magnitude of the adjustment may be different in each stimulation program to maintain current or predefined amplitude ratios between the programs. Therefore, the global adjustment may not only reduce multiple steps of programming for the patient, but also promote uniformity and reduce patient error that could result when modifying several programs with varying parameter values.

The global adjustment may be applied to a plurality of stimulation programs associated with a group of programs, a set of program groups, or all programs stored within an implantable medical device (IMD), including an implantable pulse generator (IPG), or an external programmer. Additionally, the global adjustment of a parameter may be utilized with any stimulation program parameter. As mentioned previously, example stimulation parameters may include voltage amplitude, current amplitude, pulse width, pulse rate, and electrode combination and polarity. Stimulation modification using the global adjustment is described in further detail herein.

As used in this disclosure, the term "program" may generally refer to a combination of parameter settings, including one or more of electrode combination, electrode polarity, pulse amplitude (current or voltage), pulse width and pulse rate, used to provide stimulation therapy. A program of stimulation therapy may be delivered alone or in combination with other programs, e.g., simultaneously via multiple stimulation channels or on a time-interleaved basis via one or more stimulation channels. The term "group," as used in this disclosure, may generally refer to a therapeutic stimulation therapy including one or more programs. For example, the programs in a group may be delivered, as described above, simultaneously or on a time-interleaved basis. In other words, the programs in a group of programs are delivered together in combination with one another.

FIG. 1 is a conceptual diagram illustrating an exemplary stimulation system 10 with an external programmer 20 in conjunction with patient 12. System 10 includes an implantable medical device (IMD) 14 including an implantable pulse generator (IPG) that delivers electrical stimulation therapy to patient 12 and a programmer 20 for programming IMD 14. IMD 14 delivers stimulation therapy to patient 12 via leads 16A and 16B (collectively "leads 16"). Leads 16 may, as shown in FIG. 1, be implanted proximate to spinal cord 18 of patient 12 to deliver spinal cord stimulation (SCS) therapy to patient 12. Spinal cord stimulation may be used, for example, to reduce pain experienced by patient 12.

Although an implantable IMD 14 is described for purposes of illustration, various embodiments of this disclosure also may be applicable to external medical devices that reside outside the patient's body, and deliver electrical stimulation therapy using one of more implanted leads deployed via a percutaneous port. For example, the functions of IMD 14 may be combined with the functions of programmer 20 into one external device that provides stimulation therapy. SCS therapy will be described for purposes of illustration. However, IMD 14 and leads 16 may also be placed anywhere with patient 12 to treat any of a variety of conditions including but not limited to chronic pain, tremor, Parkinson's disease, epilepsy, neuralgia, urinary or fecal incontinence, sexual dysfunction, obesity, or gastroparesis. In addition, in some embodiments, IMD 14 may be configured as a microstimulator or array of microstimulators equipped with electrodes, in which case one or both leads 16A, 16B may be eliminated. Accordingly, FIG. 1 is provided for purposes of illustration.

In the example of FIG. 1, IMD 14 may deliver stimulation therapy to patient 12 according to one stimulation group at a time, i.e., an active group. The active group may contain one or more programs. As discussed previously, a stimulation program may specify values for a number of parameters associated with stimulation therapy delivered via an electrode configuration. The parameters may include stimulation pulse voltage or current amplitudes, pulse widths, pulse rates, electrode combinations, and other appropriate parameters such as duration or duty cycle. Leads 16 each include one or more electrodes (not shown). The program further specifies an electrode configuration in terms of electrodes that have been selected to deliver pulses according to the program and the polarities of the selected electrodes. Not all electrodes may function at any given time. The parameters may vary in value between stimulation programs.

IMD 14 also may deliver stimulation therapy to patient 12 according to a plurality of programs for a single symptom area, such as a number of leg pain programs. The plurality of programs for the single area may be a part of a program group for therapy. IMD 14 may have different program parameters for each of the leg pain programs based on a position of patient 12, an activity rate of patient 12, or other patient parameters. For example, IMD 14 may deliver stimulation therapy to patient 12 during a first leg pain program using a first parameter value, e.g. a voltage amplitude. In a second leg pain program, another first parameter value for voltage amplitude may be used. Patient 12 may be using the first leg pain program and desire to adjust the amplitude to increase the stimulation therapy. Patient 12 may increase the amplitude by using external programmer 20 to globally change the first parameter value in both the first leg pain program and in the second leg pain program to corresponding second parameter values. The second parameter value in the first leg program may be adjusted to a different magnitude than the second parameter value in the second leg program to maintain an amplitude ratio between the first and second leg pain programs or maintain the change between the first and second parameter value in each program with respect to the available change, or range, in each program. In this manner, patient 12 does not need to manually adjust the parameters associated with each individual program within the program group. Instead, the parameter adjustment may be applied globally to all programs within the program group.

External programmer 20 allows a user, such as a physician or patient, to optimize the stimulation therapy provided by IMD 14. External programmer 20 may be a so-called clinician programmer, primarily operated by a clinician to program IMD 14, or a so-called patient programmer, primarily operated by the patient to select programs or make parameter adjustments. Programmer 20 allows the user to adjust stimulation parameters to customize stimulation throughout therapy. Once the clinician initially creates stimulation programs for patient 12, patient 12 may use programmer 20 as desired to change parameters to create a more efficacious stimulation therapy.

Patient 12 may find that one or more stimulation programs provide effective treatment. Programmer 20 provides a user interface (not shown in FIG. 1) for the user to select a currently effective program from one or more program groups. Each group may include one or more programs that provides therapy to an anatomical location, e.g., a leg or pelvic region, to overcome pain, or some other organizational scheme designed to manage stimulation programs for patient 12. Patient 12 may navigate through program groups, programs within a program group, or individual stimulation parameters using the user interface. The user interface may also indicate to patient 12 when and to what magnitude the global adjustment has been changed.

Programmer 20 controls IMD 14, e.g., by instructions delivered via wireless telemetry, to modify or adjust parameters of stored stimulation programs. Once IMD 14 receives instructions to adjust a stimulation parameter, the active stimulation group will begin delivering therapy with the new parameters. In this manner, patient 12 may customize stimulation therapy in real time. All of programs and program groups may be stored in the IMD 14. Alternatively, in some embodiments, the programs and program groups may be stored in external programmer 20, in which case the programmer may selectively download programs or groups to the IMD 14 for operation.

The invention is not limited to the combination of leads 16 shown in FIG. 1. For example, system 10 may include only a single lead or more than two leads implanted proximate to spinal cord 18. Furthermore, as mentioned previously, the invention is not limited to the delivery of SCS therapy. For example, one or more leads 16 may extend from IMD 14 to the brain (not shown) of patient 12, and IMD 14 may deliver deep brain stimulation (DBS) therapy to patient 12 to treat tremor or epilepsy. As further examples, one or more leads 16 may be implanted proximate to the pelvic nerves (not shown) or stomach (not shown), and IMD 14 may deliver stimulation therapy to treat incontinence or gastroparesis.

While any stimulation parameters may be modified or adjusted through the use of a global, multi-program adjustment, voltage amplitude will be the stimulation parameter used as an example in this disclosure for purposes of illustration. Therefore, parameter values will be associated with the voltage amplitude. Parameter values for voltage amplitude will be referred to as amplitude values. Again, similar adjustments may be made to pulse width, pulse rate, and electrode combination and/or polarity.

Figure 2:
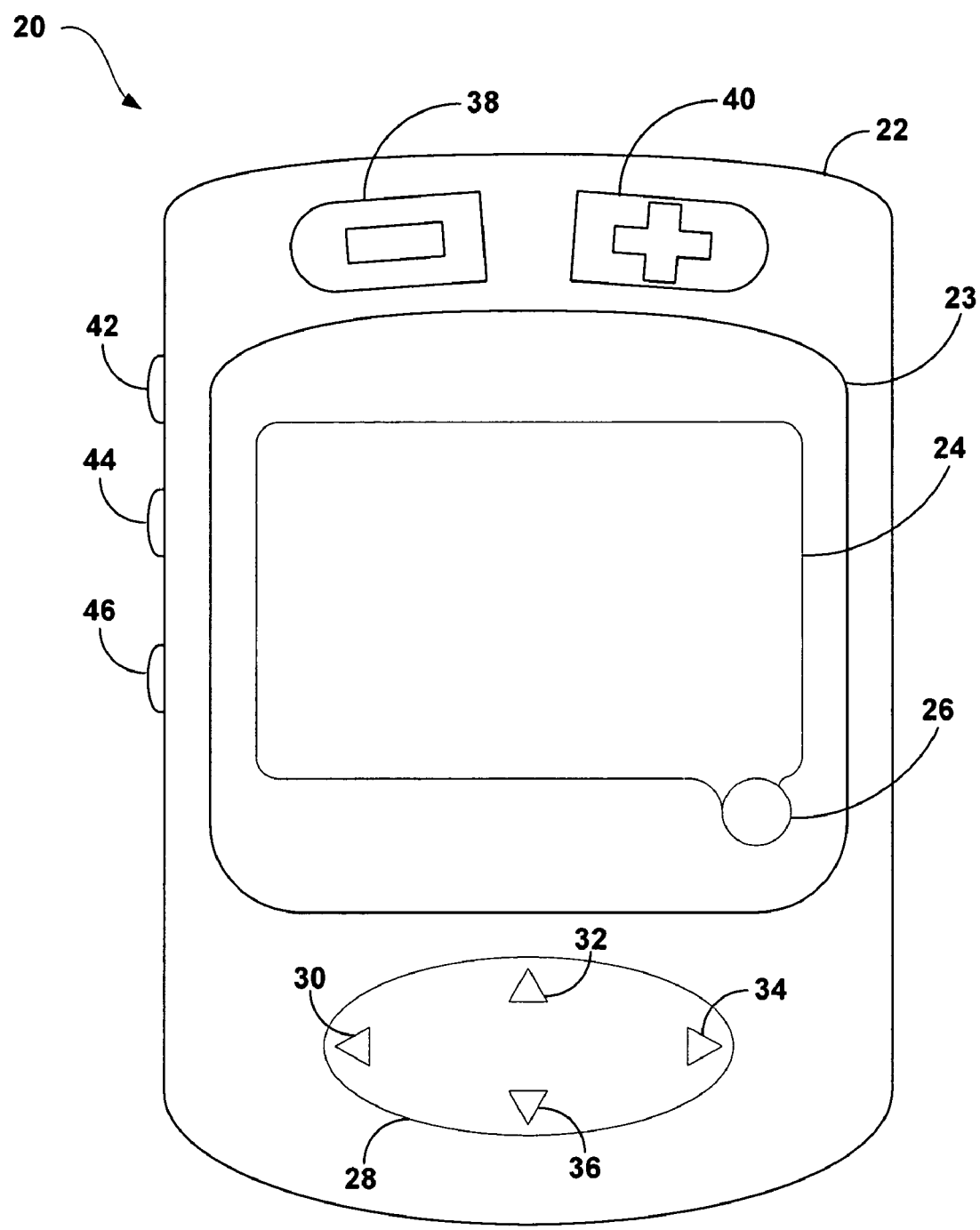
FIG. 2 is a conceptual diagram illustrating an exemplary external programmer that controls stimulation therapy.

FIG. 2 is a conceptual diagram illustrating an exemplary external programmer that controls stimulation therapy. As shown in FIG. 2, external programmer 20 provides a user interface for a user, such as patient 12, to modify stimulation therapy. Programmer 20 is protected by a housing 22 which encloses circuitry necessary for the programmer to operate. Programmer 20 also includes display 24, power button 26, increase button 40, decrease button 38, and select buttons 42, 44, and 46. Cover 23 protects screen 24 from being damaged during programmer 20 use. Programmer 20 also includes control pad 28 which allows a user to navigate through items displayed on display 24 in the direction of arrows 30, 32, 34 and 36.

Programmer 20 is a hand held device that may accompany patient 12 at all times. Housing 22 may be constructed of a polymer, metal alloy, composite, or combination material suitable to protect and contain components of programmer 20. In addition, housing 22 may be partially or completely sealed such that fluids, gases, or other elements may not penetrate the housing and affect components therein. Power button 26 may turn programmer 20 on or off as desired by patient 12. Power button 26 may also control the illumination level, or backlight level, of display 24. In some embodiments, power button 26 may be a knob that rotates clockwise and counter-clockwise to control programmer 20 operational status and illumination level of display 24. Programmer 20 is prevented from turning off during telemetry with IMD 14 or another device to prevent the loss of transmitted data or the stalling of normal operation. Alternatively, programmer 20 and IMD 14 may include instructions which handle possible unplanned telemetry interruption, such as battery failure or inadvertent device shutdown.

Display 24 may be a liquid crystal display (LCD) or similar monochrome or color display capable of providing information to patient 12. Display 24 may provide information regarding current stimulation therapy, an active group of stimulation programs, and operational status of programmer 20. Control pad 28 allows patient 12 to navigate through items displayed on display 24. Patient 12 may press control pad 28 on any of arrows 30, 32, 34, and 36 in order to move to another item on display 24 or move to another screen not currently shown on the display. In some embodiments, pressing the middle of control pad 28 may select any item highlighted in display 24. In other embodiments, scroll bars, a touch pad, scroll wheel, individual buttons, or a joystick may perform the complete or partial function of control pad 28.

Decrease button 38 and increase button 40 provide an input mechanism for patient 12. In general, decrease button 38 may decrease the value of a highlighted stimulation parameter one step every time the decrease button is pressed. In contrast, increase button 40 may increase the value of a highlighted stimulation parameter one step every time the increase button is pressed. While buttons 38 and 40 may be used to control the value of any stimulation parameter, buttons 38 and 40 may control only voltage amplitude unless patient 12 performs certain steps that allow buttons 38 and 40 to control a different parameter such as current amplitude, pulse width, or pulse rate. In other embodiments, control pad 28 may be the only input that patient 12 may use to navigate through the screens and menus of programmer 20.

Decrease button 38 and increase button 40 may function as global adjustments that change the voltage amplitude in all programs within a group with the press of one button. In this case, voltage amplitude may be considered a global parameter when applied to stimulation programs associated within one group. Alternatively, the global adjustment may be applied to some or all groups containing stimulation programs. When the global adjustment is applied to more than one group, patient 12 may select the groups to be affected by the global adjustment. In some embodiments, global adjustment may be limited to an active group, i.e., a group with programs that are then being used to deliver stimulation to patient 12.

In an example embodiment, pressing increase button 40 or decrease button 38 once will change the value of the voltage amplitude one step in every stimulation program of an active program group. In this manner, patient 12 may avoid separately changing the voltage amplitude in each program on an individual basis to keep therapy amplitudes consistent. Instead, the same parameters in each program will be adjusted. The multi-program parameter adjustment may be applied to all programs in an active group, as described above. Alternatively, in some embodiments, the patient 12 may select one or more programs within a group, e.g., by marking, checking, or otherwise selecting the programs via the user interface, and then apply the parameter adjustment to such programs.

A multi-program, global adjustment may avoid inaccurate changes in parameter magnitudes that could result between stimulation programs when the parameters are manually changed by patient 12 for each individual program. Global adjustment ensures that parameter changes are propagated to all selected programs or all programs in an active group. In addition, the parameter adjustments may be normalized for each individual program. In particular, the adjustment step may vary between programs and is set according to predefined rules governing global adjustments. These rules may be provided by a physician or set based upon the type of therapy and will be further defined below. For example, some programs may have different adjustment step sizes, maximum, cumulative adjustments, or parameter minima or maxima.

Select buttons 42, 44, and 46 may be configured to perform operational functions related to stimulation therapy or the use of programmer 20. For example, buttons 42 and 44 may control the volume of audible sounds produced by programmer 20, wherein button 42 increases the volume and button 44 decreases the volume. Button 46 may be pressed to enter an operational menu that allows patient 12 to configure the user interface of programmer 20 to the desires of patient 12. For example, patient 12 may be able to select a language, backlight time, display 24 brightness, or other similar options. In alternative embodiments, buttons 38 and 40 may control all operational and selection functions, such as those related to audio volume or stimulation therapy.

Programmer 20 may take other shapes or sizes not described herein. For example, programmer 20 may take the form of a clam-shell shape, similar to cellular phone designs. When programmer 20 is closed, some or all elements of the user interface may be protected within the programmer. When programmer 20 is opened, one side of the programmer may contain a display while the other side may contain input mechanisms. In any shape, programmer 20 may be capable of performing the various parameter adjustment functions described herein.

In alternative embodiments, the buttons of programmer 20 may perform different functions than the functions provided in FIG. 2. In addition, other embodiments of programmer 20 may include different button layouts or different numbers of buttons. For example, programmer 20 may even include a single touch screen that incorporates all user interface functionality.

Figure 3:
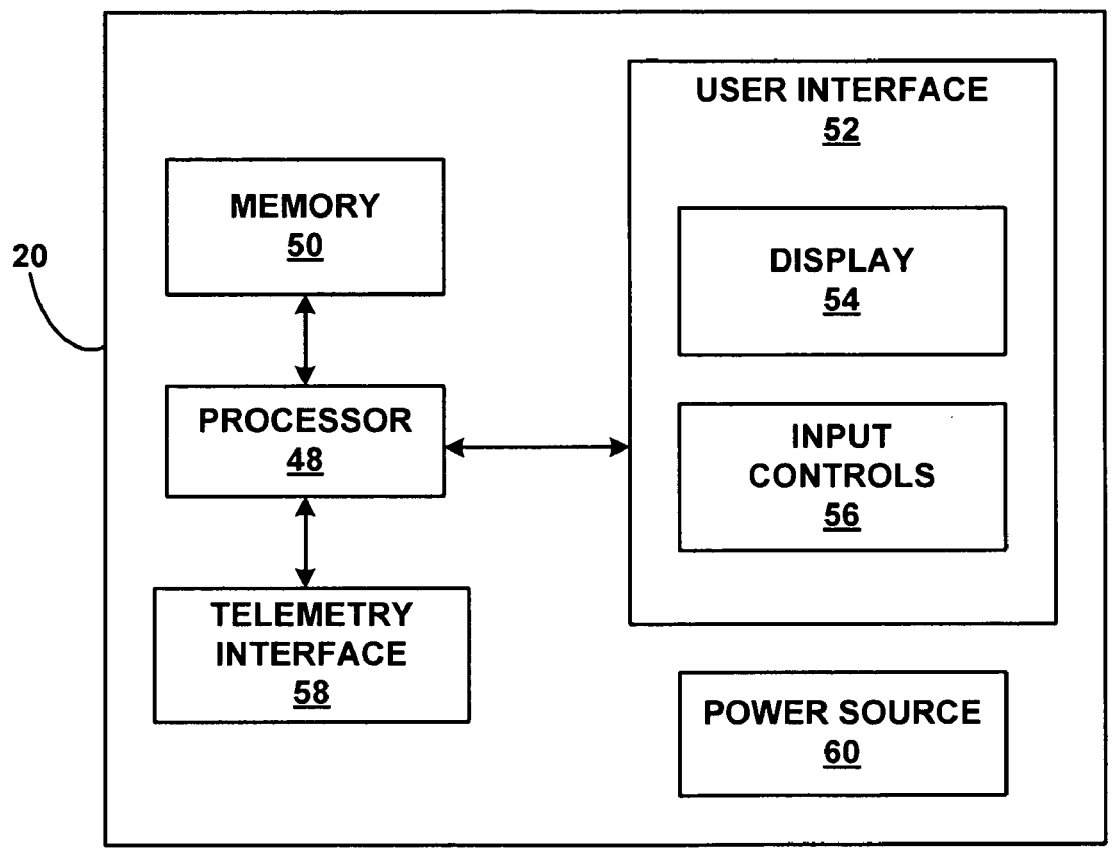
FIG. 3 is functional block diagram illustrating components of an exemplary external programmer.

FIG. 3 is functional block diagram illustrating components of an exemplary external programmer 20. As shown in FIG. 3, external programmer 20 includes processor 48, memory 50, user interface 52, wireless telemetry interface 58, and power source 60. Programmer 20 may be used to select stimulation programs, generate new stimulation programs, modify stimulation programs through individual or global adjustments, and transmit the new programs to IMD 14. As described herein, programmer 20 allows a stimulation parameter in stimulation programs of a group to be changed by a global adjustment. Programmer 20 may be one of a patient programmer or a physician programmer. A physician programmer may include more functionality than the patient programmer to control every aspect of IMD 14.

A user, either a physician or patient 12, may interact with programmer 20 through user interface 52. User interface 52 includes a display 54, such as an LCD or other screen, to show information related to stimulation therapy and input controls 56 to provide input to programmer 20. Input controls 56 may include the buttons described in FIG. 2. Processor 48 monitors activity from input controls 56 and controls display 54 or stimulation function accordingly. In some embodiments, the display may be a touch screen that enables the user to select options directly from the display screen. For example, the user may select programs or groups of programs for application of global parameter adjustments. In other embodiments, user interface 52 also includes audio circuitry for providing audible instructions or sounds to patient 12 and/or receiving voice commands from patient 12.

Memory 50 may include instructions for operating user interface 52, telemetry interface 44 and managing power source 60. Memory 50 also includes instructions defining global adjustment functionality for changing a stimulation parameter of multiple programs simultaneously. These adjustment instructions may include a set of rules that vary depending upon the type of stimulation therapy or desires of the clinician. In addition, memory 50 may store all stimulation programs programmed and their original and most recent set of parameter values. Memory 50 may include any one or more of a random access memory (RAM), read-only memory (ROM), electronically-erasable programmable ROM (EEPROM), flash memory, or the like. Memory 50 may also include a removable memory portion that may be used to provide memory updates or increases in memory capacities. A removable memory may also allow sensitive patient data to be removed before programmer 20 is used by a different patient. Processor 48 may comprise any one or more of a microprocessor, digital signal processor (DSP), application specific integrated circuit (ASIC), field-programmable gate array (FPGA), or other digital logic circuitry.

Wireless telemetry in programmer 20 may be accomplished by radio frequency (RF) communication or proximal inductive interaction of external programmer 20 with IMD 14. This wireless communication is possible through the use of telemetry interface 58. Accordingly, telemetry interface 58 may be similar to the telemetry interface contained within IMD 14. Telemetry interface 58 may function according to communication protocols defined by instructions stored in memory 50. Telemetry interface 58 may communicate with IMD 14 regarding global adjustments in separate commands for each program being adjusted, as a wrapper for the individual group adjustment commands, or as one command covering all programs to be adjusted. Methods for communicating global adjustments to IMD 14 may be governed by system 10 functionality, power conservation, or the implementation of the global adjustment. In alternative embodiments, programmer 20 may be capable of direct communication through a wired connection. In this manner, other external devices may be capable of communicating with programmer 20 without needing to establish a secure wireless connection.

Power source 60 delivers operating power to the components of implantable programmer 20. Power source 60 may include one or more batteries and a power generation circuit to produce the operating power. In some embodiments, a rechargeable battery may be used to allow extended operation. Recharging may be accomplished by connecting power source 60 to a cradle or plug that is connected to an alternating current (AC) outlet. In addition, recharging may be accomplished through proximal inductive interaction between an external charger and an inductive charging coil within programmer 20. In other embodiments, one or more nonrechargeable batteries may be used. In addition, programmer 20 may be directly coupled to an alternating current outlet to operate. Power source 60 may include circuitry to monitor power remaining within a battery. In this manner, display 24 may provide a current battery level indicator or low battery level indicator when the battery needs to be replaced or recharged. In some cases, power source 60 may be capable of estimating the remaining time of operation using the current battery.

A clinician may configure programmer 20 to limit the availability of global adjustments to patient 12. For example, the clinician may prohibit patient 12 from using any independent parameter or global adjustment at any time or only under certain circumstances. In other cases, the clinician may only allow individual parameter adjustments. In some cases, the clinician may only allow global adjustments without allowing individual parameter adjustments. In the preferred embodiment, programmer 20 is programmed to allow patient 12 to individually or globally adjust stimulation parameters. Configuration of programmer 20 may be made by a clinician either directly or via a clinician programmer that programs the IMD 14 and, optionally, patient programmer 20.

Figure 4A:
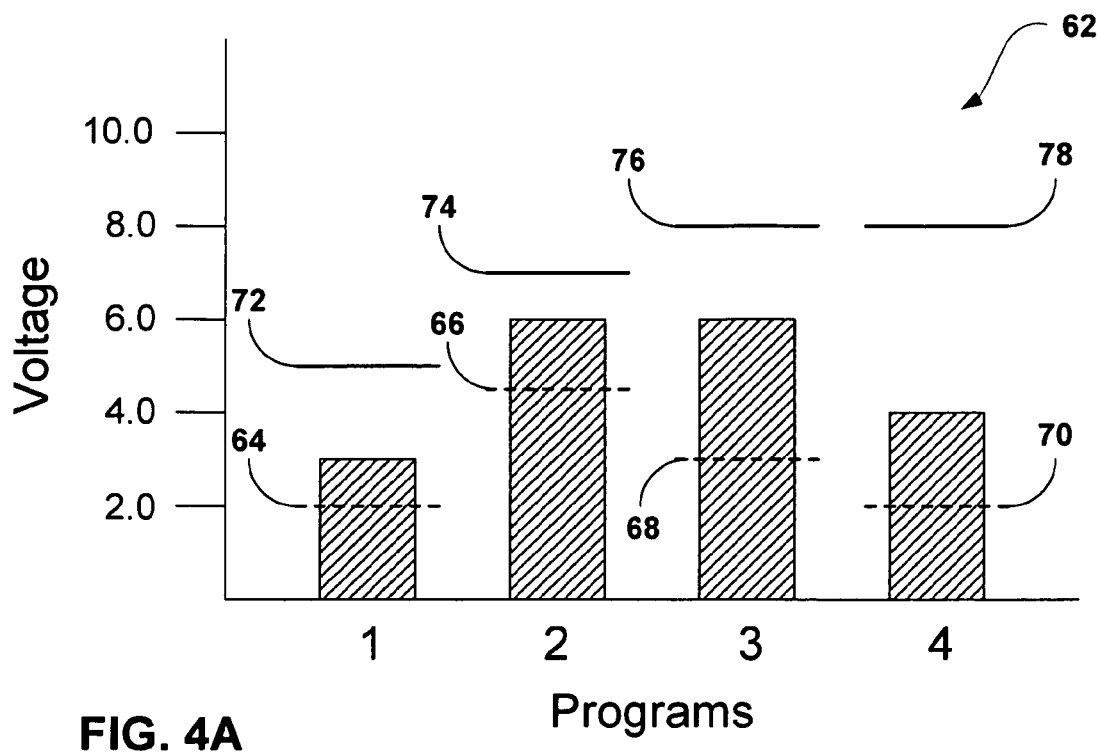
FIGS. 4A and 4B are exemplary graphs of stimulation voltage for multiple stimulation programs.
Figure 4B:
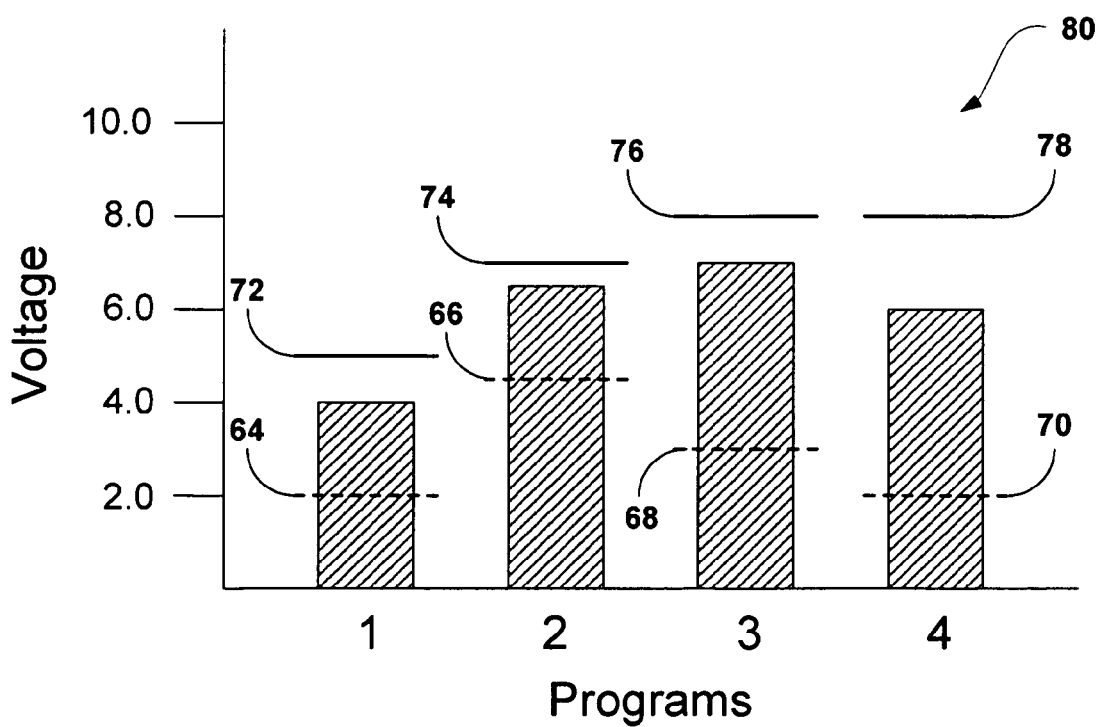

FIGS. 4A and 4B are exemplary graphs of stimulation voltage amplitudes for multiple stimulation programs. In the example of FIG. 4A, initial voltage amplitudes of four different stimulation programs 1, 2, 3, and 4 are shown in graph 62 prior to global adjustment. Voltage, in volts, is located along the y-axis while the programs are located along the x-axis. Programs 1, 2, 3, and 4 may be part of an exemplary group A. Group A is considered an active group if one of its programs is currently being used to deliver stimulation therapy, or if one of its programs is selected for therapy if stimulation is not currently being delivered. In some embodiments, more or less programs may be a part of one group. In addition, one or multiple groups of stimulation programs may be stored within IMD 14 or programmer 20.

The voltage amplitude of each program is shown at a first voltage amplitude, i.e., a first parameter value, before patient 12 desires to change the amplitude. In the example of FIG. 4A, program 1 is set to 3.0 volts, program 2 is set to 6.0 volts, program 3 is set to 6.0 volts, and program 4 is set to 4.0 volts.

Each program 1, 2, 3, and 4 may have an associated maximum and minimum voltage amplitude limit associated with it. These limits are set such that patient 12 will not encounter uncomfortable stimulation past the maximum limit nor receive stimulation below the minimum limit that is known to be effective. Minimum limits 64, 66, 68, and 70 are associated with programs 1, 2, 3, and 4, respectively. Maximum limits 72, 74, 76, and 78 are associated with programs 1, 2, 3, and 4, respectively. The difference between the maximum limit and the minimum limit is referred to as the operating range, and the difference between a limit and the first parameter value is referred to as the adjustment range. The limits for each parameter may be set in the factory or by the clinician. In some cases, patient 12 may modify a limit. However, patient 12 control may be restricted to only reducing the limit, i.e., to a more comfortable voltage.

As an example, the operating range for program 1 is 5.0 volts minus 2.0 volts, or 3.0 volts. This 3.0 volt range is the total voltage range in which patient 12 may set the voltage amplitude for program 1. If patient 12 desires to increase the voltage amplitude, the upward adjustment range is 5.0 volts minus the present voltage amplitude (3.0 volts), or 2.0 volts. In this case, the voltage amplitude of program 1 may be increased 2.0 volts before the amplitude is limited by maximum limit 72. If patient 12 desires to decrease the voltage amplitude, the downward adjustment range is 3.0 volts minus 2.0 volts, or 1.0 volt. In this case, the voltage amplitude of program 1 may be decreased 1.0 volts before the amplitude is limited by minimum limit 64. Operating ranges and adjustment ranges may be similarly calculated for each of the other programs 2, 3, and 4.

While maximum limits 72, 74, 76, and 78 and minimum limits 64, 66, 68, and 70 vary among stimulation programs 1, 2, 3, and 4, some or all of the limits may be the same. In addition, any minimum limit 64, 66, 68, or 70 may be set to zero volts while any maximum limit 72, 74, 76, or 78 may be set to 10.0 volts. While system 10 may only be capable of providing voltage amplitudes of 10.0 volts in the example of FIG. 4A, maximum limits 72, 74, 76, or 78 may be set to the maximum voltage amplitude that system 10 may deliver to patient 12.

Patient 12 may use programmer 20 to apply a global adjustment to the voltage amplitude of programs 1-4 of group A. Pressing increase button 40 once will increase the voltage amplitude of programs 1-4 one step, and pressing decrease button 38 will decrease the voltage amplitude of programs 1-4 one step. The step for each program may be of equal or varying amplitude, dependent on the predetermined rules governing global adjustment.

FIG. 4B is a graph 80 depicting the voltage amplitudes of stimulation programs 1-4 after patient 12 has utilized global adjustment to increase the voltage amplitude of each program. In this example, patient 12 has increased the voltage amplitude by a particular amount. In response, the global adjustment feature has increased the voltage amplitude of each program 1-4 by the same percentage of the adjustment range for each program. In other words, the adjustment range for each program was divided by a resolution value (the same resolution value for each program) to calculate a step value. The step value is an increment specific to each program. For each time patient 12 presses increase button 40, the voltage amplitude of each program 1-4 increases by the step value. Alternatively, the number of times increase button 40 is pressed may be multiplied by the step value to arrive at the change value, where the change value represents the difference between the first voltage shown in FIG. 4A, the first parameter value, and the second voltage shown in FIG. 4B, the second parameter value.

As an example, the voltage amplitude change for program 1 resulting from the global adjustment will be calculated. Program 1 has a first voltage amplitude of 3.0 volts. It is assumed that maximum limit 72 for program 1 is set at 5.0 volts. Therefore, the adjustment range is equal to 2.0 volts. The resolution value in the example of FIG. 4B is 10, which results in a step value of 0.2 volts over the 2.0 volt adjustment range. In this example, patient 12 presses increase button 40 five times to result in a change value of 1.0 volts, i.e., 5 steps multiplied by 0.2 volts/step. The change value is added to the first voltage amplitude (3.0 volts) for program 1 to result in a second voltage amplitude of 4.0 volts (3.0 volts plus 1.0 volt) for program 1.

Programs 2-4 are similarly changed on a global basis to result in each second voltage amplitude shown in graph 80. In should be noted that the resolution value for all programs affected by the global adjustment is identical. However, the step value varies according to the available adjustment range for each program. In this manner, the voltage amplitude of programs 1-4 is changed to maintain the same percentage change with respect to the available adjustment range for each program. Similarly, the voltage amplitude of programs 1-4 may decrease according to how many times decrease button 38 is pressed. Step values may be any value supported by system 10. For example, the smallest step value may be 0.2 volts as described in the above example or lower step values such as 0.1 or 0.05 volts. Alternatively, the supported step value may be determined by the clinician during initial programming of programmer 20. For example, the clinician may limit system 10 to a coarse step value of 0.2 volts or a fine step value of 0.05 volts.

In the example of FIG. 4A, the upward adjustment ranges for programs 2, 3, and 4 are 1 volt (7.0 volts minus 6.0 volts), 2 volts (8 volts minus 6 volts), and 4 volts (8 volts minus 4 volts), respectively. Therefore, if patient 12 presses increase button 40 five times, the step size for programs 2, 3, and 4 are 0.1 volts, 0.2 volts, and 0.4 volts, respectively. Again, the step size is a function of the adjustment range divided by the resolution. In this case, the adjustment ranges for programs 2, 3, and 4 (1, 2 and 4 volts, respectively) are divided by the resolution (10). Consequently, the global increases resulting from entry of five increase steps by patient 12, given the applicable adjustment ranges and resolutions, produce second voltage amplitudes of 1 volt, 0.5 volts, 1.0 volts, and 2.0 volts for programs 1, 2, 3, and 4, respectively.

Each time either increase button 40 or decrease button 38 is pressed, a timer may start that defines a window of time patient 12 has to press the respective button again and keep the same step value. After the window expires, a new step value may be calculated when performing the global adjustment. In some cases, the adjustment range may become very small, such that the calculated step size is smaller than programmer 20 or IMD 14 can produce. In this case, the step size may be limited to the smallest step size capable by system 10. If one program reaches its respective maximum limit before other programs, this program may stop changing voltage amplitude at the limit while the other programs continue to change. Alternatively, all programs may stop changing voltage amplitude once one of the programs reaches its maximum limit.

In an alternative embodiment, the adjustment range may be equal to the operating range, which is equal to the difference between the maximum limit and the minimum limit. In this case, the step value is constant within each program for increases or decreases. In addition, the resolution value may vary between programs, depending on the desires of the clinician or patient 12. Essentially, the step value or resolution value for each program may be assigned any value independently of another program, as determined by the clinician.

In other embodiments, the step value for each program within a group may be a fixed value that does not vary between programs 1-4. In this manner, the voltage amplitude for each program would change with the same step value, without regard to the first voltage amplitude, operating range, or adjustment range. If one program reaches its respective maximum limit before other programs, this program may stop changing voltage amplitude at the limit while the other programs continue to change. Alternatively, all programs may stop changing voltage amplitude once one of the programs reaches its maximum limit.

In an alternative embodiment, the global adjustment may cause the voltage amplitude of each stimulation program to change proportionately to one another. In this embodiment, the global adjustment will change the voltage amplitude of each stimulation program such that the ratios of each voltage will remain constant while using the global adjustment. One of the plurality of stimulation programs is selected to determine a ratio for each of the other programs to use for the global adjustment.

In this alternative embodiment, the selected program may be the program currently used to deliver stimulation or the program with the largest voltage amplitude. Essentially, the step value of the selected program is calculated to match the ratio of the first voltage amplitude values of each program in the group so that the second voltage amplitudes of each program are proportional to the first voltage amplitudes. Again, the "first" voltage amplitude refers to the initial amplitude prior to an increase or decrease, while the "second" voltage amplitude refers to the amplitude following an increase or decrease.

In other embodiments, the step value may not be fixed in a global adjustment sequence. The step value may be varied as the voltage becomes further from one limit or closer to another limit. For example, an algorithm may be applied to the step value such that the step value is large as the voltage is increased from the minimum limit and the step value decreases in size as the voltage reaches the maximum limit. The algorithm may simply be an exponential or logarithmic algorithm or a more complex ramping equation tailored to the specific parameters of each program. In this manner, patient 12 may finely tune voltage, or other stimulation parameters, as the voltage amplitude approaches the maximum or minimum limits. The method of changing step values may be applied to a step value at any point within the range, not just a continued sequence of global adjustments. In additional embodiments, the lower limit may be a measured perception threshold and the upper limit may be a measured discomfort threshold. Each threshold is measured based upon feedback from patient 12. The range between the perception threshold and the discomfort threshold is the usable range, where the usable range defines the range of voltages that patient 12 may select. Each program limit may be calibrated in this manner and the step value for each program may be calculated based upon the usable range. When patient 12 uses the global adjustment, each program is adjusted according to the specific usable range for each program.

Hence, adjustment may include measuring a perception threshold for each of the programs, measuring a discomfort threshold for each of the programs, and determining an adjustment range for each of the programs based upon an existing parameter value and one of the measured perception threshold and the measured discomfort threshold. The adjustment range for each of the programs is then divided by a resolution value to determine a respective step value. Application of the adjustment may then include applying the respective step values to the programs.

As an example, processor 48 determines the adjustment range of the currently used stimulation program, which would make it the selected program. The adjustment range is divided by a resolution value of, e.g., 10, to determine the step value. The step value is the increment in which the first voltage value is increased, or decreased, with each press of button 40 or 38. The step value is multiplied by the number of increments selected to result in a change value.

The ratio used to determine the step value for each of the other stimulation programs in the group is based upon the first voltage amplitude of each stimulation program. The first voltage amplitude of each stimulation program is divided by the first voltage amplitude of the selected program. The result is the ratio that is multiplied by the step value, or change value, to determine the scaled change value for each program. Each scaled change value is added to the first voltage amplitude of each program to result in the second voltage amplitude of each program. In this manner, the voltage amplitudes of all programs within the group remain at the same ratios after global adjustments.

In the case that the global adjustment would cause the voltage amplitude of a program in the group to exceed the maximum limit or fall below the minimum limit, the voltage amplitude of that program would remain at the limit while other programs continue to be adjusted according to the global adjustment. The ratio of the voltage amplitudes for the programs in the group may be stored such that the correct ratios may be restored if the voltage amplitudes are adjusted in the opposite direction. In alternative embodiments, the adjustment of all programs within the group may stop once one program reaches its respective limit.

Other embodiments not explicitly described herein may be used when using the global adjustment of system 10. In some other cases, the global adjustment may be extended to programs within other selected groups or all groups stored in system 10, instead of a single group. Moreover, the global adjustment may also be used with other stimulation parameters such as current amplitude, pulse width, pulse rate, or electrode combinations or polarities.

Figure 5:
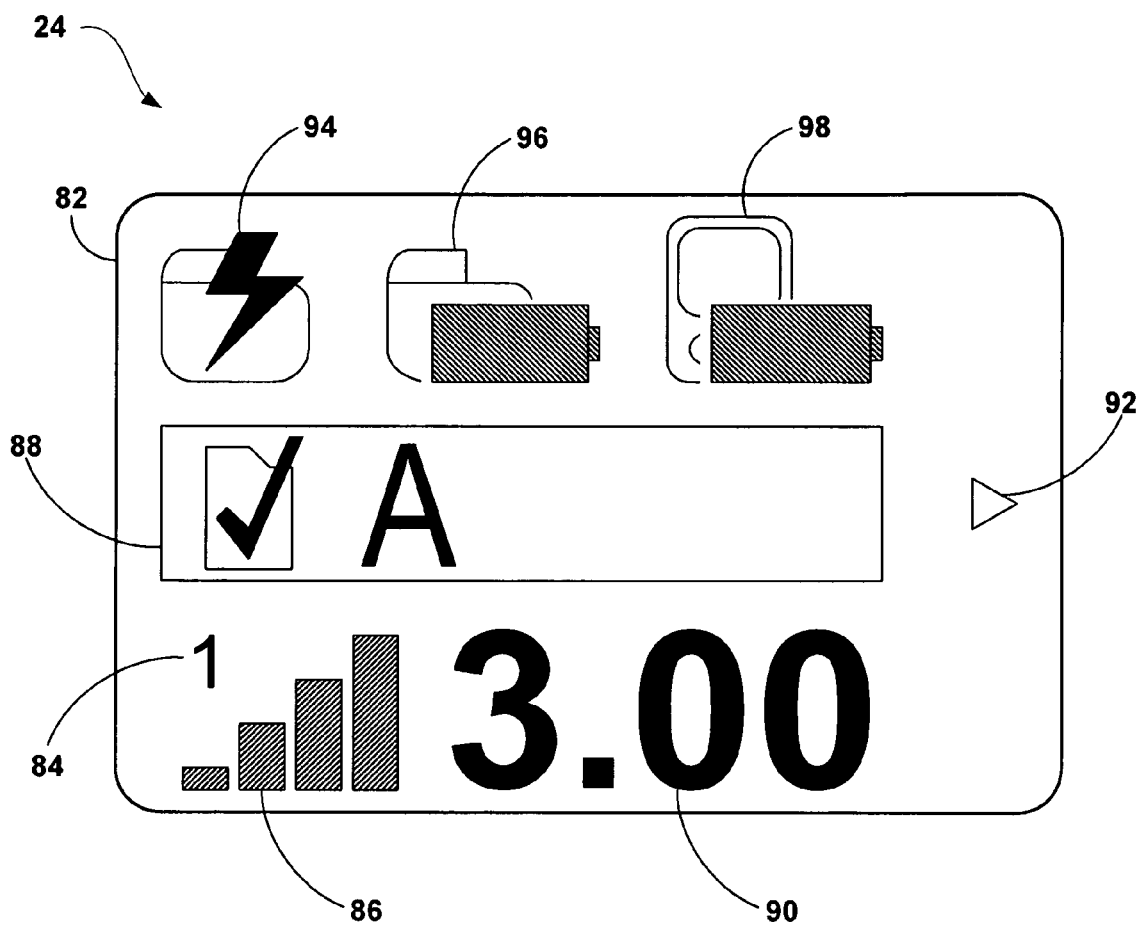
FIG. 5 is a conceptual diagram illustrating an exemplary screen shot associated with a single stimulation program.

FIG. 5 is a conceptual diagram illustrating an exemplary screen shot associated with a single stimulation program presented by programmer 20. In the example of FIG. 5, display 24 of programmer 20 provides screen 82 to a user, such as patient 12. Screen 82 includes program number 84, parameter icon 86, group box 88, voltage amplitude 90, navigation arrow 92, stimulation icon 94, IMD battery 96, and programmer battery 98. Screen 82 is meant to provide information to patient 12 regarding stimulation status. More or less information may be provided to patient 12, as desired by the clinician or patient.

Program number 84 and parameter icon 86 indicate the stimulation program that is associated with the current group. In the example of FIG. 5, the program is part of group A. Programmer 20 may be capable of containing up to 26 groups that include a total of 32 programs. In some embodiments, one group may contain no more than 4 programs. In other embodiments, programmer 20 may be capable of containing more or less programs or groups of programs. Each group may include more or less than four programs. This capability may be limited by the size or format of memory 50.

Group box 88 contains information regarding the group shown on screen 82. Group box 88 indicates that group "A" is being shown and currently selected as the group to provide stimulation by the checked file icon within the group box. In some embodiments, group box 88 may contain different information. For example, the groups may be numbered instead of having letter identities or the current amount of time for which the group has been used may be indicated.

Voltage amplitude 90 displays the current voltage amplitude of the selected program 1 of group A. In the example of FIG. 5, the voltage amplitude is shown to be at 3.00 volts. If the voltage amplitude is at a maximum or minimum limit, a limit icon (not shown) may be displayed. In other embodiments, voltage amplitude 90 may present more or less decimal places as necessary for the stimulation therapy. In alternative embodiments that use current amplitude, pulse rate, or pulse width as a global adjustment, those parameter values may be displayed in place of voltage amplitude 90. In addition, patient 12 may navigate to show the value of any desired parameter.

Stimulation icon 94 indicates the current status of stimulation therapy. Currently, the lightning bolt is shown to indicate that stimulation is being delivered to patient 12. In the case that stimulation is not being delivered, the bolt in icon 94 may not be shown. IMD battery 96 indicates the status of the battery in IMD 14, which currently indicates that the battery is fully charged, or has a full charge in the case that the battery is not rechargeable. In other embodiments of IMD battery 96, a percentage of battery life or battery life time remaining may be shown. Similar to IMD battery 96, programmer battery 98 indicates the status of the battery in programmer 20. Currently, programmer battery 98 displays that the programmer battery has a full charge. In alternative embodiments, other status indications may be used to show a percentage or time remaining of the programmer battery.

Arrow 92 provides a method for patient 12 to navigate to another screen of display 24. Patient 12 may highlight arrow 92 and select it to move to another screen. In a similar manner, patient 12 may highlight other icons areas of screen 82 to make modifications to that particular portion of the stimulation therapy. The components of screen 82 are provided as an exemplary screen for a single program, while other layouts or arrangements of screen 82 may be possible as well. Screen 82 may also show some elements in color if display 24 supports a color screen.

Figure 6:
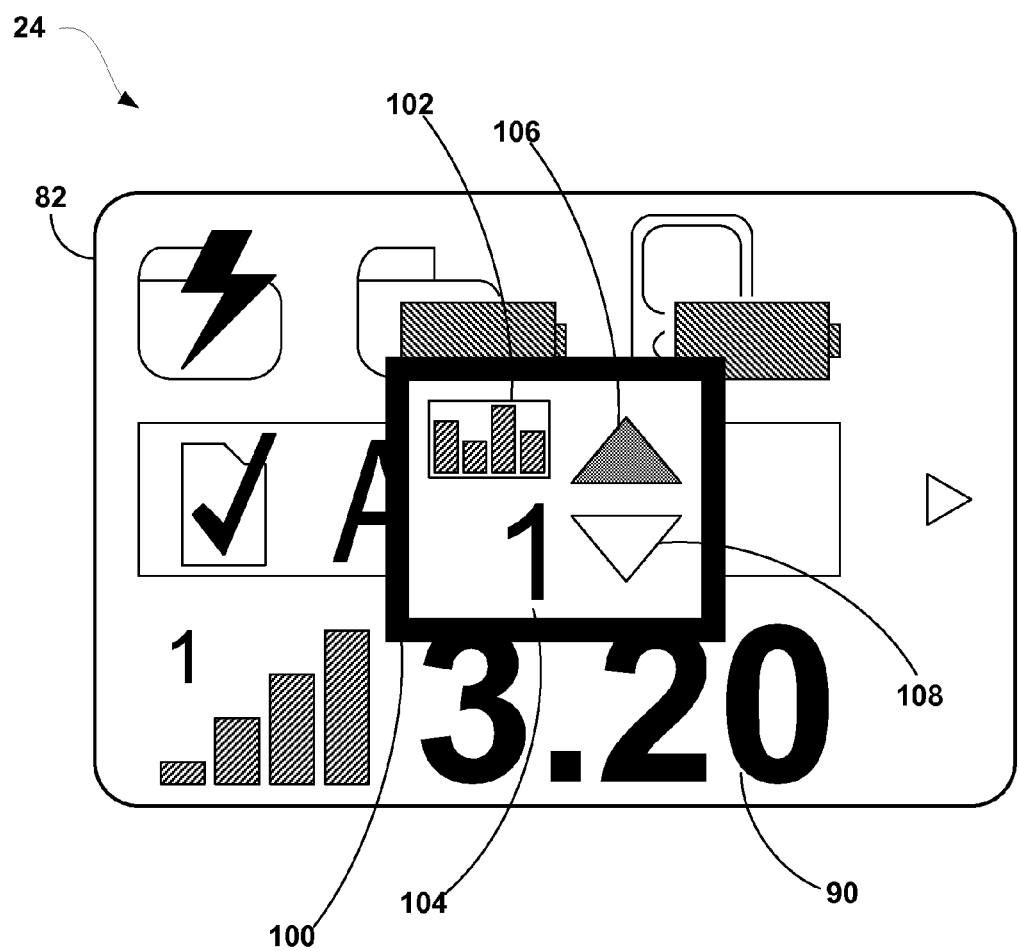
FIG. 6 is a conceptual diagram illustrating an exemplary screen shot associated with a single stimulation program with a pop-up screen indicating a global parameter adjustment.

FIG. 6 is a conceptual diagram illustrating an exemplary screen shot associated with a single stimulation group with a pop-up screen indicating a global parameter adjustment. As shown in FIG. 6, screen 82 of display 24 includes pop-up window 100 that indicates a global adjustment has been made to the programs of group A. Pop-up window 100 includes global icon 102, parameter variable 104, increase indicator 106 and decrease indicator 108.

Pop-up window 100 appears over screen 82 anytime that patient 12 chooses to make a global adjustment. The pop-up window may appear for a predetermined period of time, such as 3, 5, or 10 seconds. During the period that pop-up window 100 is presented, the step value calculated for the programs in the group may stay the same. Therefore, patient 12 may continue to increase or decrease the voltage amplitude at the same step value.

Global icon 102 indicates to patient 12 that a global adjustment has been made, i.e., that the voltage amplitude for all programs in group A has been changed. Parameter variable 104 indicates the number of times patient 12 has selected to increase or decrease the voltage amplitude. In other words, parameter variable 104 is the number of increments or decrements made to the voltage amplitude of each program in group A. Increase indicator 106 is highlighted to indicate that the global adjustment has made an increase to the voltage amplitude. Decrease indicator 108 would be highlighted if the voltage amplitude was selected to be decreased.

In the example of screen 82, patient 12 has pressed increase button 40 once to increase the voltage amplitude of the programs of group A one step, as the voltage amplitude of program 1 has increased to 3.20 volts. If patient 12 presses increase button 40 more times, parameter variable 104 will indicate the number of times button 40 has been pressed. Patient 12 may also press decrease button 38 to reduce the voltage amplitude globally.

In this case, parameter variable 104 would decrease as many times as button 38 is pressed. If decrease button 38 is pressed more than increase button 40 was pressed, decrease indicator 108 would become highlighted and parameter variable 104 would indicate the number of steps the global adjustment has been decreased. In some embodiments, a plus or minus sign may be displayed next to parameter variable 104 to indicate an upward or downward change relative to a current parameter value.

Patient 12 may continue to make global adjustments, increasing or decreasing the voltage amplitude of programs in group A as desired. Once the time of the global adjustment period has expired, pop-up window 100 may disappear over screen 82. After this time, further global adjustments may require a recalculation of step values for each program in the group. In other embodiments, pop-up window 100 may cover more or less of screen 82. Alternatively, no pop-up window 100 may appear when patient 12 makes a global adjustment.

The multi-program, global parameter adjustment feature may be locked in patient programmer 20 by a clinician so that the patient can either only use the global adjustment feature, or cannot use global adjustment and must use individual adjustment. Alternatively, the patient 12 may be allowed to select either global or individual parameter adjustment, e.g., by interaction with the user interface presented by programmer 20. As a further alternative, when patient 12 makes an adjustment, a modal message may be presented to ask the patient whether a global adjustment is desired. In this case, the patient 12 clicks on a global or individual parameter adjustment indication. As another example, global icon 102 may be configured, particularly in a touchscreen environment, so that the patient 12 can select global or individual parameter adjustment by clicking or re-clicking on the global icon to turn global adjustment on and off.

Figure 7:
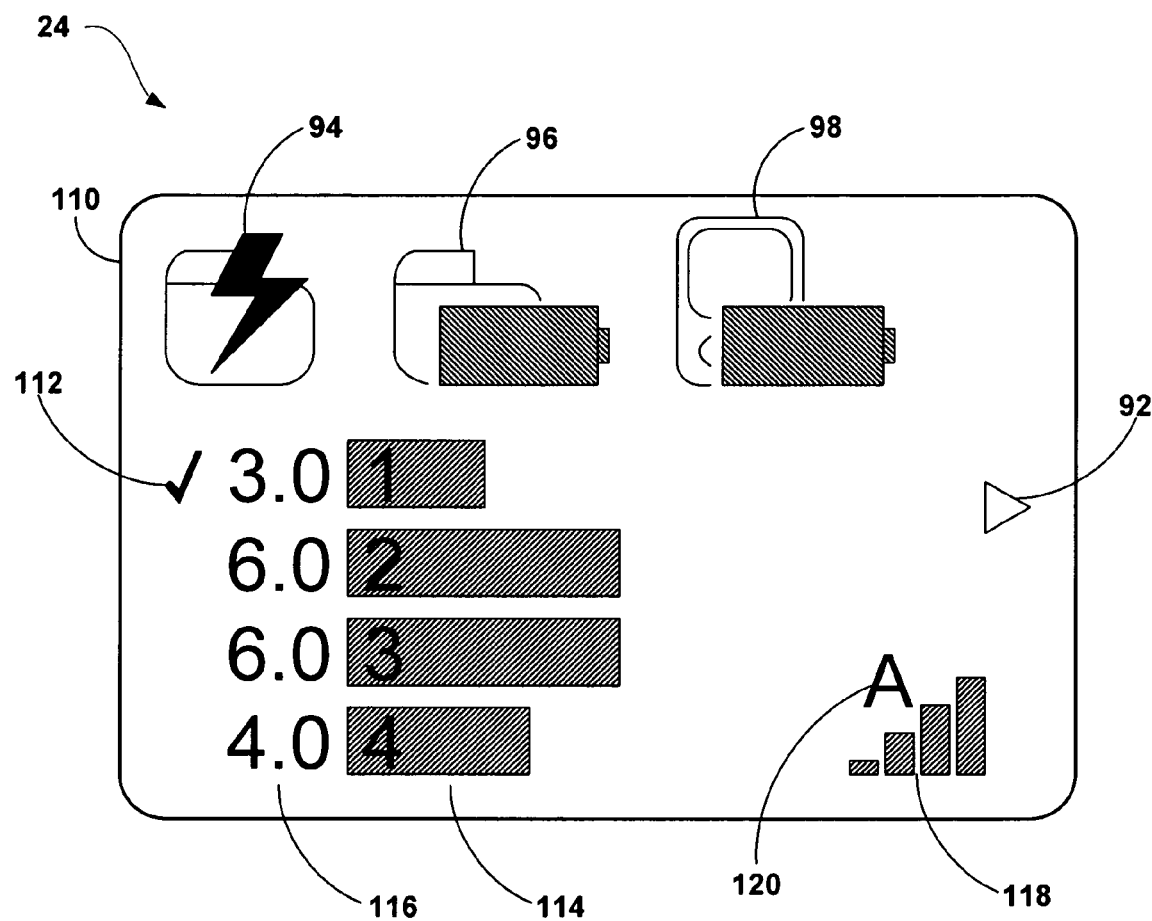
FIG. 7 is a conceptual diagram illustrating an exemplary screen shot associated with a group of stimulation programs.

FIG. 7 is a conceptual diagram illustrating an exemplary screen shot associated with a group of stimulation programs. In the example of FIG. 7, screen 110 of display 24 provides information to patient 12 regarding all four programs within group A. Screen 110 includes check 112, graph 114, voltage amplitude 116, parameter icon 118, and group number 120. Arrow 92, stimulation icon 94, IMD battery 96, and programmer battery 98 are the same elements provided in screen 82 of FIG. 6.

Check 112 indicates that program 1 has been selected for parameter adjustment. In the global parameter adjustment mode, however, the parameter adjustment made to program 1 will be propagated to other programs in the same group, i.e., programs 2, 3, and 4 in Group A. Graph 114 provides a graphical indication of the voltage amplitude of each program 1-4. Voltage amplitude 116 provides the numerical indication of the voltage amplitude of each program 1-4. Similar to screen 82, parameter icon 118 and group number 120 are indicators of the currently selected group for stimulation therapy.

Patient 12 may navigate screen 110 and choose stimulation therapy from another program of group A or another program from a different group within programmer 20. Patient 12 may also choose to display stimulation parameters other than voltage amplitude. Screen 110 is provided as a way to quickly view programs 1-4 of group A. In other embodiments, more stimulation parameters of each program may be displayed on screen 110. In some embodiments, the information of screen 110 may be presented in a different layout or arrangement.

Figure 8:
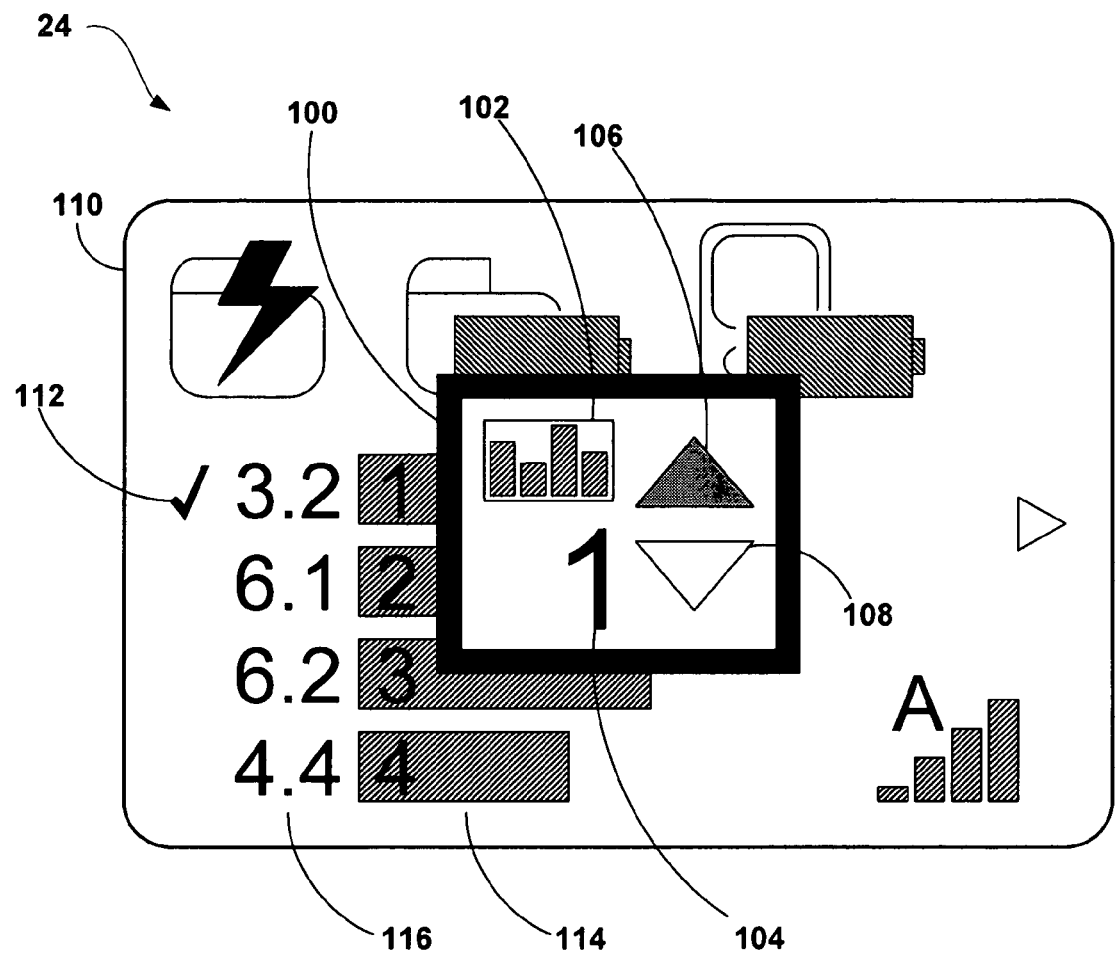
FIG. 8 is a conceptual diagram illustrating an exemplary screen shot associated with a group of stimulation programs with a pop-up screen indicating a global parameter adjustment.

FIG. 8 is a conceptual diagram illustrating an exemplary screen shot associated with a group of stimulation programs with a pop-up screen indicating a global parameter adjustment. As shown in FIG. 8, screen 110 of display 24 includes pop-up window 100 that indicates a global adjustment has been made to the programs of group A. Pop-up window 100 includes global icon 102, parameter variable 104, increase indicator 106 and decrease indicator 108, where pop-up window 100 is the same pop-up window used to appear over screen 82.

Pop-up window appears over screen 110 anytime that patient 12 chooses to make a global adjustment. The pop-up window may appear for a predetermined period of time, such as 3, 5, or 10 seconds. During the period that pop-up window 100 is presented, the step value calculated for the programs in the group may stay the same. Therefore, patient 12 may continue to increase or decrease the voltage amplitude at the same step value.

Global icon 102 indicates to patient 12 that a global adjustment has been made, i.e., that the voltage amplitude for all programs in group A has been changed. Parameter variable 104 indicates the number of times patient 12 has selected to increase or decrease the voltage amplitude. In other words, parameter variable 104 is the number of increments or decrements made to the voltage amplitude of each program in group A. Increase indicator 106 is highlighted to indicate that the global adjustment has made an increase to the voltage amplitude. Decrease indicator 108 would be highlighted if the voltage amplitude was selected to be decreased.

In the example of screen 110, patient 12 has pressed increase button 40 once to increase the voltage amplitude of the programs of group A one step, as the voltage amplitude of program 1 has increased to 3.2 volts, program 2 has increased to 6.1 volts, program 3 has increased to 6.2 volts, and program 4 has increased to 4.4 volts. Graph 114 also increases to represent the parameter values shown in voltage amplitude 116. The operation of the global adjustment is identical to that described in FIG. 6. In other embodiments, pop-up window 100 may cover more or less of screen 110. Alternatively, no pop-up window 100 may appear when patient 12 makes a global adjustment.

In other embodiments, graph 114 may display the voltage amplitudes as a relative value instead of an absolute value. For example, the minimum limit may be shown as an empty bar and the maximum limit may be shown as a full bar. In this manner, the bars may change size depending on the voltage resolution and the voltage range. The relative value bars may provide a better indication of available voltage adjustment to patient 12. In particular, a relative value indication such as a bar may change at different rates based on resolution and range.

Figure 9:
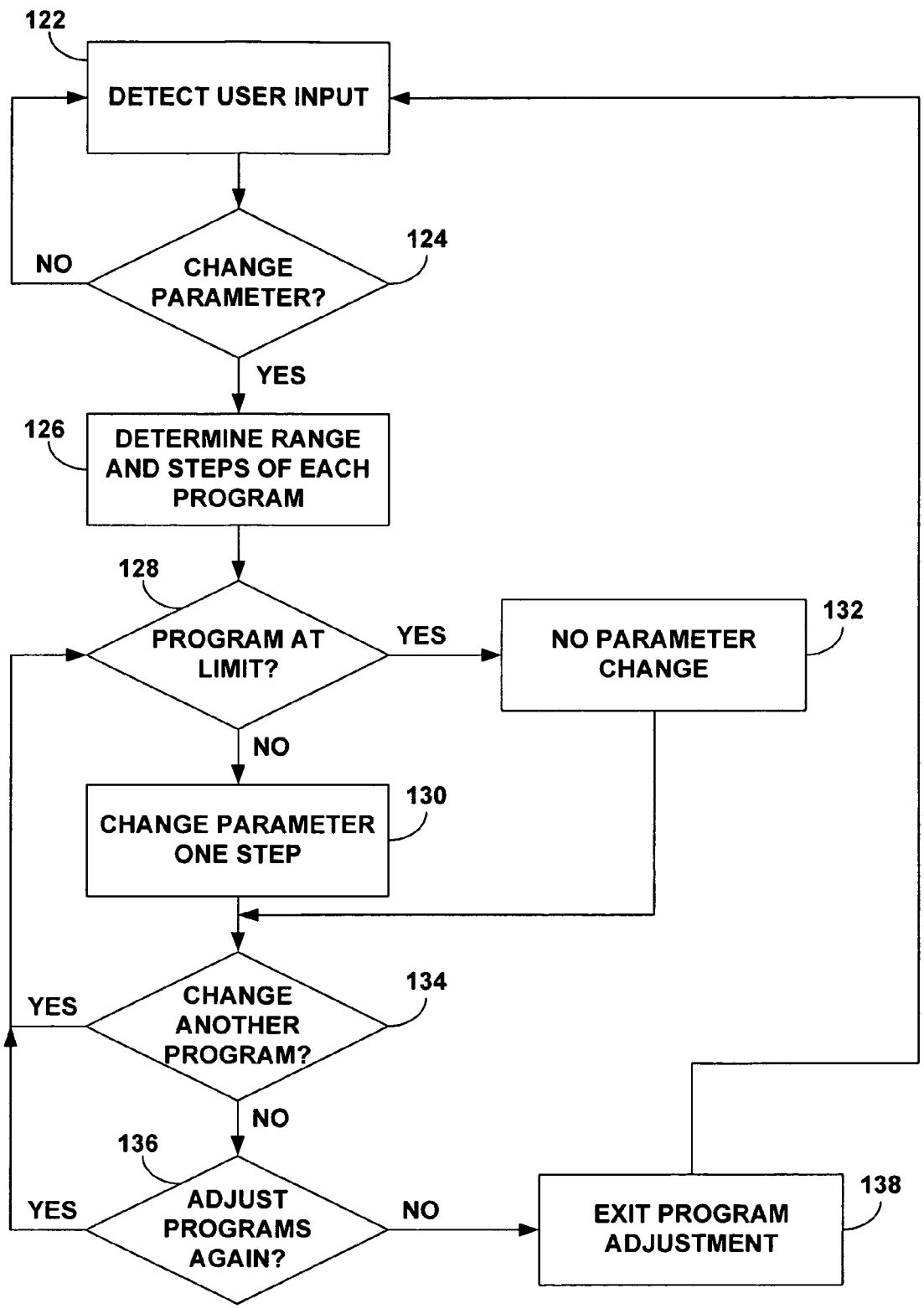
FIG. 9 is a flow diagram illustrating an exemplary technique for adjusting a parameter for all stimulation programs.

FIG. 9 is a flow diagram illustrating an exemplary technique for adjusting a parameter for all stimulation programs. In the example of FIG. 9, processor 48 of programmer 20 follows a method of adjusting a stimulation parameter, such as the voltage amplitude, according to the global adjustment. Processor 48 waits to detect user input for a global adjustment (122). If processor 48 determines that a global change to a parameter has been initiated (124), processor 48 moves forward. If processor 48 does not receive an indicator for a global change, the processor continues to detect user input (122).

Once the global adjustment has been initiated, processor 48 determines the adjustment range and step values for each program within the group selected (126). Processor 48 then goes through the programs to be adjusted. If the program is not at a predetermined limit (128), processor 48 adjusts the voltage amplitude, or other specified parameter, one step (130). If the program is at the predetermined limit, no voltage amplitude change is made (132). After the program has been changed if possible, processor 48 determines if another program in the group needs to be adjusted (134). If there is another program to be adjusted, processor 48 makes further adjustments to other programs. If no other programs need to be adjusted, processor 48 determines if patient 12 has signaled another global adjustment (136). If processor 48 needs to make another global adjustment to the programs of the selected group, processor 48 moves to step 128. If no more global adjustments have been signaled, processor 48 exits the program adjustment method for the global adjustment (138). Subsequently, processor continues to detect user input associated with a global adjustment signal (122).

The method of adjusting a parameter globally may vary slightly in different embodiments of system 10. In another embodiment, step 126 may simply be to determine the preset step value for each program. In this embodiment, each program has a preset step value that is not changed throughout stimulation therapy.

In an alternative embodiment, step 126 may vary from the previous two embodiments. Step 126 may instead include processor 48 determining the ratios of first parameter values of each program to retain the voltage amplitude ratios as the global adjustment is made. This ratio, as described herein, is used to calculate step values for each program in the group. Step 130 may include this calculated step in the alternative embodiment.

In other embodiments of FIG. 9, the adjustment of programs may be stopped if one program reaches its predetermined limit. If this occurs, processor 48 may issue a limit indication to patient 12 that notifies the patient that no more adjustments may be made due to a limit being reached. In addition, the method may include timers to manage the time patient 12 has to continue making global adjustments to the group of programs under the current step values.

Although the disclosure may be especially applicable to the simulation of the spinal cord, the invention alternatively may be applied more generally to any type of stimulation wherein the parameters of stimulation programs may be globally adjusted to improve therapy efficacy and patient use. As examples, cortical brain stimulation, deep brain stimulation, sacral or pudendal nerve stimulation, gastric stimulation or dorsal root stimulation may benefit from programmer 20 described herein.

Various embodiments of the described invention may be implemented using one or more processors that are realized by one or more microprocessors, Application-Specific Integrated Circuits (ASIC), Field-Programmable Gate Arrays (FPGA), or other equivalent integrated or discrete logic circuitry, alone or in any combination. The processor may also utilize any of several different types of storage methods to hold computer-readable instructions for the device operation and data storage. These memory and storage media types may include a type of hard disk, random access memory (RAM), or flash memory, e.g. CompactFlash or SmartMedia. Each storage option may be chosen depending on the embodiment of the invention. While IMD 14 may contain permanent memory, external programmer 20 may contain a more portable removable memory type to enable easy data transfer or offline data analysis.

Many embodiments of the disclosure have been described. Various modifications may be made without departing from the scope of the claims. These and other embodiments are within the scope of the following claims.

The invention claimed is:

1. A system comprising:
an implantable electrical stimulator that delivers electrical stimulation; and
an external programmer comprising a processor that is configured to:
receive user input specifying an adjustment of a stimulation parameter for the implantable electrical stimulator,
determine an adjustment range for at least one of a plurality of stimulation programs based upon an existing value of the stimulation parameter and an adjustment limit of the stimulation parameter for the at least one stimulation program,
divide the adjustment range for the at least one stimulation program by a resolution value to determine at least one step value for the at least one stimulation program, wherein the at least one step value is less than the adjustment range, and
apply the adjustment based on the at least one step value to the stimulation parameter for each of the plurality of stimulation programs applied by the electrical stimulator to deliver electrical stimulation to a patient.

2. The system of claim 1, wherein each of the stimulation programs is associated with a common program group, and the implantable electrical stimulator applies the stimulation programs in the common program group in combination to deliver electrical stimulation to the patient.

3. The system of claim 1, wherein the stimulation parameter includes at least one of a stimulation amplitude, pulse width or pulse rate.

4. The system of claim 3, wherein the stimulation amplitude is one of a voltage amplitude or a current amplitude.

5. The system of claim 1, wherein the stimulator applies the plurality of stimulation programs to deliver stimulation to a patient following application of the adjustment to the stimulation parameter.

6. The system of claim 1, wherein the processor is configured to incrementally apply the adjustment based on the at least one step value to the stimulation parameter in response to multiple user inputs.

7. The system of claim 1, wherein the user input specifies an adjustment of the stimulation parameter for a selected one of the programs, and the processor applies the adjustment based on the at least one step value to the selected program, determines respective adjustments for other programs based on the specified adjustment, and applies the respective adjustments to the other programs.

8. The system of claim 1, wherein the processor determines a respective adjustment range for each of the programs based upon an existing value of the stimulation parameter and an adjustment of the stimulation parameter limit for each of the programs, divides the adjustment range for each of the programs by the resolution value to determine a respective step value for each of the programs, and applies the respective step values to the programs.

9. The system of claim 8, wherein the processor multiplies the step value for each of the programs by a number of incremental adjustments specified by the user to produce a respective overall adjustment for each of the programs, and applies the respective overall adjustments to the programs.

10. The system of claim 1, wherein the at least one program comprises a selected one of the programs, and wherein the processor is configured to:
determine the adjustment range for the selected one of the programs based upon the existing value of the stimulation parameter and the adjustment limit of the stimulation parameter for the selected program;
divide the adjustment range for the selected program by the resolution value to determine the step value;
divide an existing parameter value for each of the other stimulation programs by the existing parameter value for the selected program to determine a ratio for each of the other stimulation programs;
multiply the ratio for each of the other stimulation programs by the step value to determine respective scaled change values for each of the other stimulation programs; and
apply the step value to the existing parameter value for the selected program and apply the respective scaled change values to the existing parameter values for the other stimulation programs.

11. The system of claim 10, wherein the processor multiplies the step value for the selected program and the scaled change value for each of the other programs by a number of incremental adjustments specified by the user to produce respective overall adjustments, and applies the respective overall adjustments to the programs.

12. The system of claim 1, wherein the processor limits a value of the stimulation parameter to a predetermined limit value.

13. The system of claim 12, wherein the processor limits the stimulation parameter values for each of the programs when the stimulation parameter value for one of the programs reaches the predetermined limit value.

14. A computer-readable medium comprising instructions to cause a processor to:
receive user input specifying an adjustment of a stimulation parameter for an implantable electrical stimulator;
determine an adjustment range for at least one of a plurality of stimulation programs based upon an existing value of the stimulation parameter and an adjustment limit of the stimulation parameter for the at least one stimulation program;
divide the adjustment range for the at least one stimulation program by a resolution value to determine at least one step value for the at least one stimulation program, wherein the at least one step value is less than the adjustment range; and
apply the adjustment based on the at least one step value to the stimulation parameter for each of the plurality of stimulation programs applied by the electrical stimulator to deliver electrical stimulation to a patient.

15. The computer-readable medium of claim 14, wherein each of the stimulation programs is associated with a common program group, the implantable electrical stimulator applying the stimulation programs in the common program group in combination to deliver electrical stimulation to the patient.

16. The computer-readable medium of claim 14, wherein the stimulation parameter includes at least one of a stimulation amplitude, pulse width or pulse rate, and wherein the stimulation amplitude is one of a voltage amplitude or a current amplitude.

17. The computer-readable medium of claim 14, wherein the user input specifies an adjustment of a stimulation parameter for a selected one of the programs, and wherein the instructions cause the processor to apply the adjustment based on the at least one step value to the selected program, determine respective adjustments fin other programs based on the specified adjustment, and apply the respective adjustments to the other programs.

18. The computer-readable medium of claim 14, wherein the instructions cause the processor to:
determine a respective adjustment range for each of the programs based upon an existing value of the stimulation parameter and an adjustment limit of the stimulation parameter for each of the programs;
divide the adjustment range for each of the programs by the resolution value to determine a respective step value for each of the programs; and
apply the respective step values to the stimulation parameter for each of the respective programs.

19. The computer-readable medium of claim 18, wherein the instructions cause the processor to multiply the step value for each of the programs by a number of incremental adjustments specified by the user to produce a respective overall adjustment for each of the programs, and apply the respective overall adjustments to the stimulation parameter for each of the respective programs.

20. The computer-readable medium of claim 14, wherein the instructions cause the processor to:
determine the adjustment range for the selected one of the programs based upon the existing value of the stimulation parameter and the adjustment limit of the stimulation parameter for the selected program;
divide the adjustment range for the selected program by the resolution value to determine the step value;
divide an existing parameter value for each of the other stimulation programs by the existing parameter value for the selected program to determine a ratio for each of the other stimulation programs;
multiply the ratio for each of the other stimulation programs by the step value to determine respective scaled change values for each of the other stimulation programs; and
apply the step value to the existing parameter value for the selected program and applying the respective scaled change values to the existing parameter values for the other stimulation programs.

* * * * *

UNITED STATES PATENT AND TRADEMARK OFFICE
CERTIFICATE OF CORRECTION

| | | |
|---|---|---|
| PATENT NO. | : 7,747,330 B2 | |
| APPLICATION NO. | : 11/372354 | |
| DATED | : June 29, 2010 | |
| INVENTOR(S) | : Nolan et al. | |

It is certified that error appears in the above-identified patent and that said Letters Patent is hereby corrected as shown below:

Col. 20, Line 15: "adjustments fin other" should read --adjustments for other--

Signed and Sealed this
Third Day of May, 2011

David J. Kappos
*Director of the United States Patent and Trademark Office*